(12) United States Patent
Cosmescu

(10) Patent No.: US 12,082,864 B2
(45) Date of Patent: *Sep. 10, 2024

(54) ELECTROSURGERY BLADES WITH ARGON BEAM CAPABILITY

(71) Applicant: I.C. Medical, Inc., Phoenix, AZ (US)

(72) Inventor: Ioan Cosmescu, Phoenix, AZ (US)

(73) Assignee: I.C. Medical, Inc., Phoenix, AZ (US)

( * ) Notice: Subject to any disclaimer, the term of this patent is extended or adjusted under 35 U.S.C. 154(b) by 882 days.

This patent is subject to a terminal disclaimer.

(21) Appl. No.: 14/698,403

(22) Filed: Apr. 28, 2015

(65) Prior Publication Data

US 2016/0317209 A1 Nov. 3, 2016

(51) Int. Cl.
| | |
|---|---|
| A61B 18/14 | (2006.01) |
| A61B 18/04 | (2006.01) |
| A61B 17/3211 | (2006.01) |
| A61B 18/00 | (2006.01) |
| A61B 18/12 | (2006.01) |

(52) U.S. Cl.
CPC ........ *A61B 18/042* (2013.01); *A61B 18/1402* (2013.01); *A61B 17/3211* (2013.01); *A61B 2018/00148* (2013.01); *A61B 2018/00607* (2013.01); *A61B 2018/00994* (2013.01); *A61B 2018/1253* (2013.01); *A61B 2018/126* (2013.01); *A61B 2018/1412* (2013.01)

(58) Field of Classification Search
CPC ... A61B 17/32; A61B 18/042; A61B 18/1402; A61B 17/3211; A61B 2018/00148; A61B 2018/00607; A61B 2018/00994; A61B 2018/1412

See application file for complete search history.

(56) References Cited

U.S. PATENT DOCUMENTS

| | | | | |
|---|---|---|---|---|
| 4,589,411 | A * | 5/1986 | Friedman | A61B 18/10 331/127 |
| 5,242,442 | A * | 9/1993 | Hirschfeld | A61B 18/1402 604/35 |
| 5,318,565 | A * | 6/1994 | Kuriloff | A61B 18/1402 604/119 |
| 5,413,575 | A * | 5/1995 | Haenggi | A61B 18/1402 606/39 |
| 6,293,945 | B1 * | 9/2001 | Parins | A61B 18/1402 606/45 |
| 6,405,733 | B1 * | 6/2002 | Fogarty | A61B 90/39 128/899 |
| 2001/0018586 | A1 * | 8/2001 | Cosmescu | A61B 18/1402 606/48 |
| 2003/0176858 | A1 * | 9/2003 | Marshall | A61B 18/1402 606/41 |
| 2004/0024392 | A1 * | 2/2004 | Lewis | A61L 29/041 606/22 |
| 2005/0273097 | A1 * | 12/2005 | Ryan | A61B 18/1442 606/45 |

(Continued)

*Primary Examiner* — Jaymi E Della
(74) *Attorney, Agent, or Firm* — Zeman-Mullen & Ford, LLP

(57) ABSTRACT

An electrode assembly with an electrosurgery blade having argon beam capabilities. The electrode assembly includes an electrosurgery blade, which may be monopolar, bipolar, or bipolar with monopolar capability, and a non-conductive housing for providing an ionized argon gas.

23 Claims, 5 Drawing Sheets

(56) References Cited

U.S. PATENT DOCUMENTS

| | | | | |
|---|---|---|---|---|
| 2006/0259031 A1* | 11/2006 | Carmel | .............. | A61B 18/1402 |
| | | | | 606/41 |
| 2007/0191759 A1* | 8/2007 | Stoller | ................. | A61B 1/3132 |
| | | | | 604/22 |
| 2008/0119836 A1* | 5/2008 | Littrup | ............... | A61B 18/0218 |
| | | | | 606/21 |
| 2009/0069802 A1* | 3/2009 | Garito | .................... | A61B 18/14 |
| | | | | 606/45 |
| 2010/0274236 A1* | 10/2010 | Krimsky | ............ | A61B 18/0218 |
| | | | | 606/21 |
| 2013/0177695 A1* | 7/2013 | Podhajsky | ......... | A61B 18/1442 |
| | | | | 427/2.11 |
| 2013/0204241 A1* | 8/2013 | Baust | ................. | A61B 18/082 |
| | | | | 606/24 |
| 2014/0350555 A1* | 11/2014 | Heard | ................ | A61B 18/1485 |
| | | | | 606/49 |
| 2015/0359585 A1* | 12/2015 | Weber | ................ | A61B 18/1402 |
| | | | | 606/49 |

\* cited by examiner

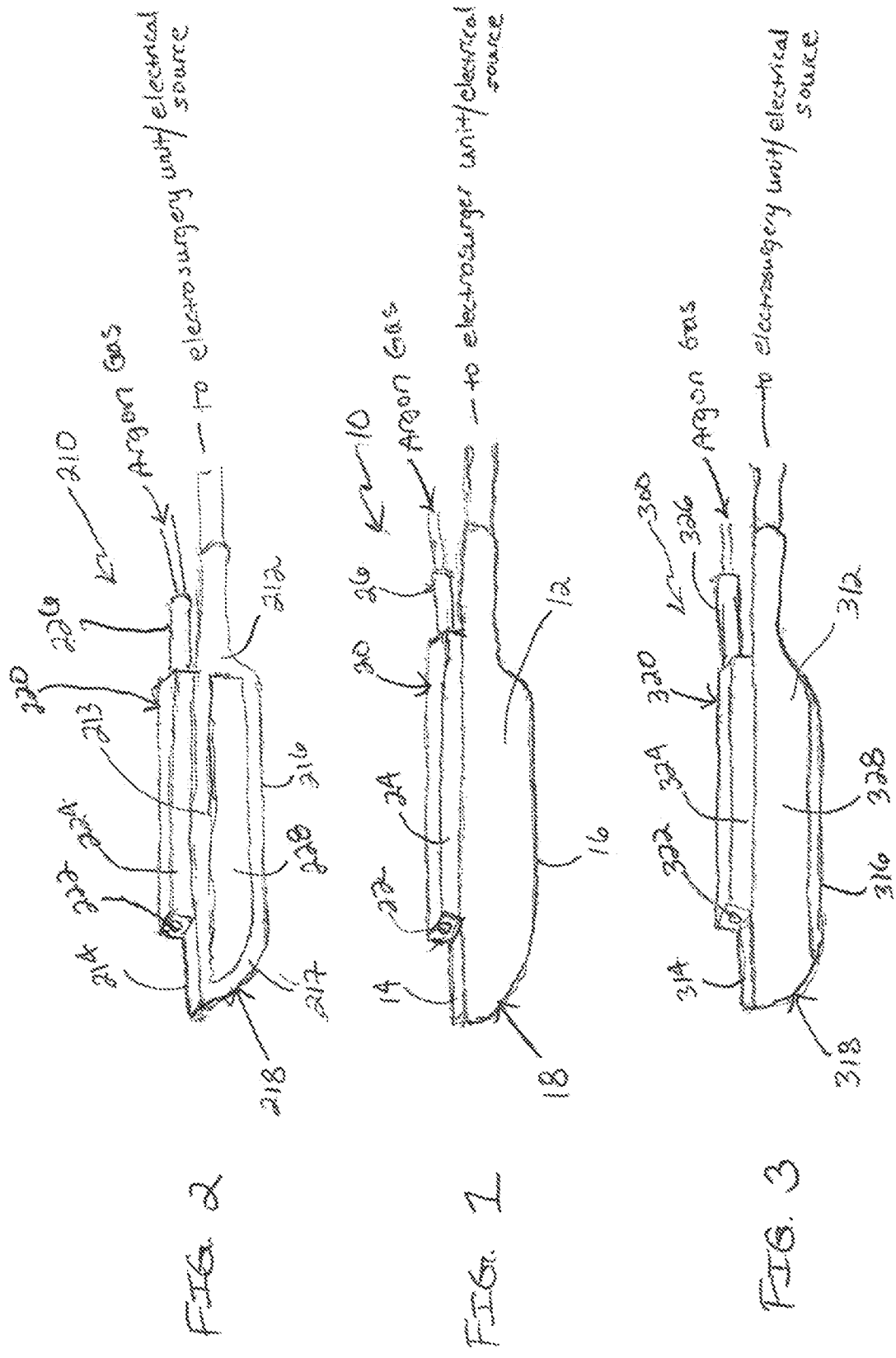

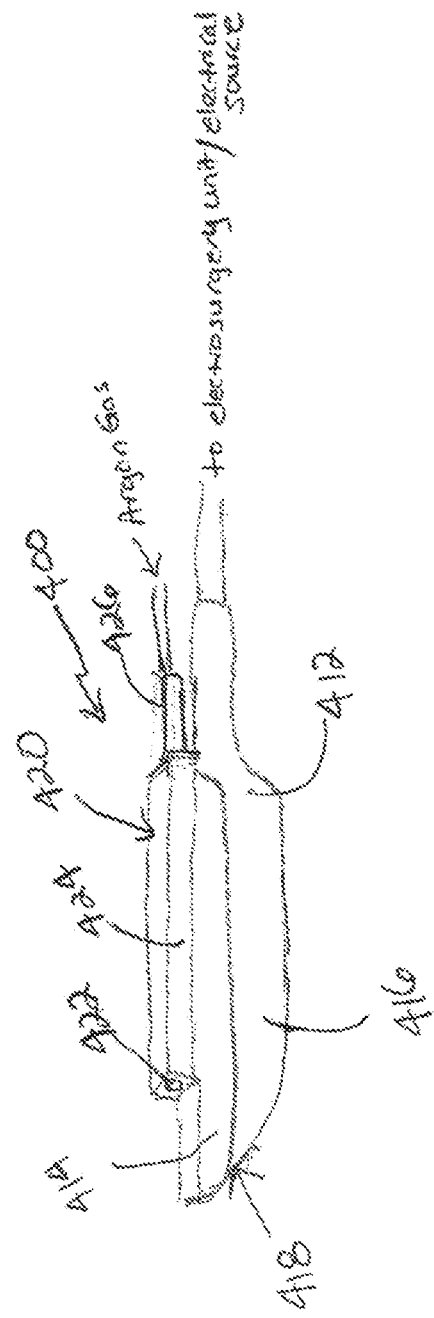

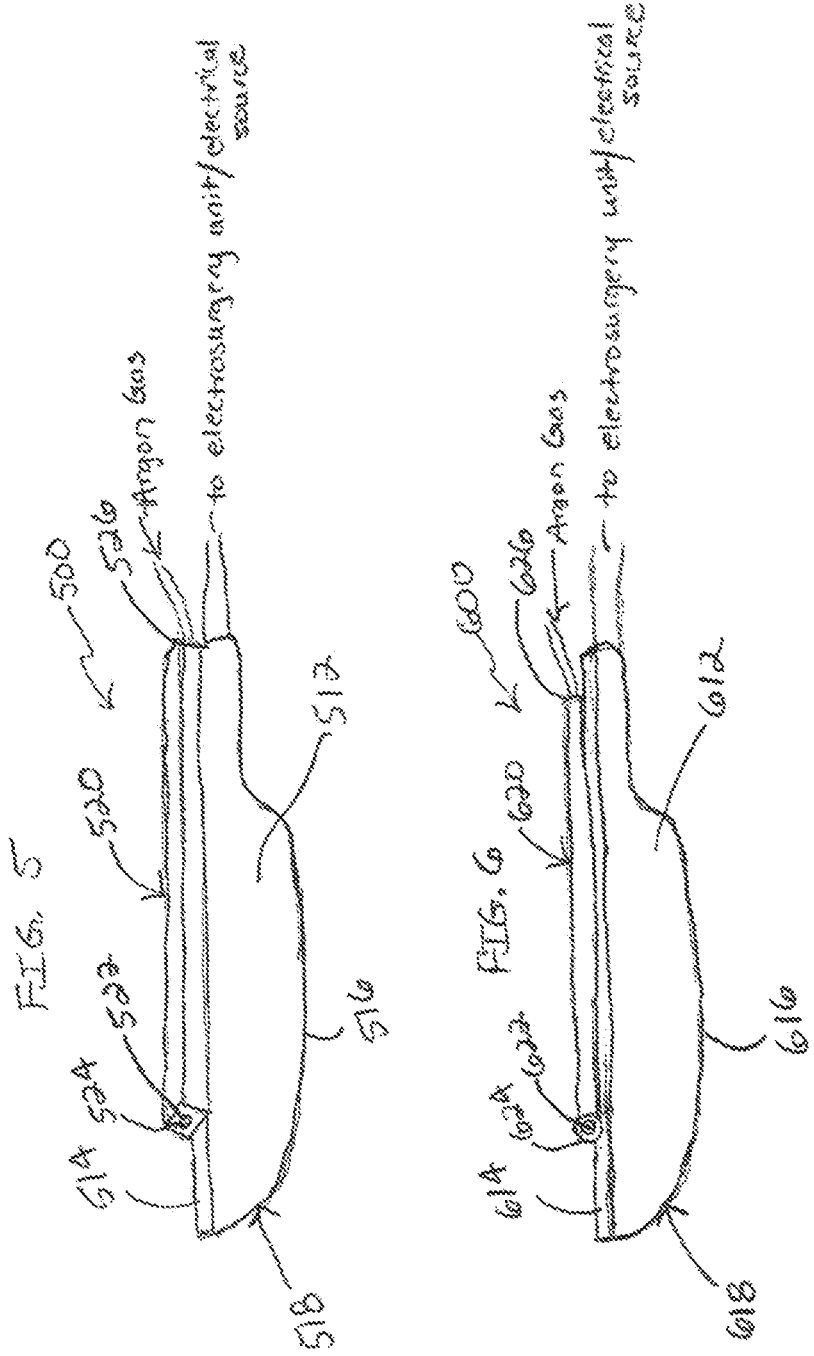

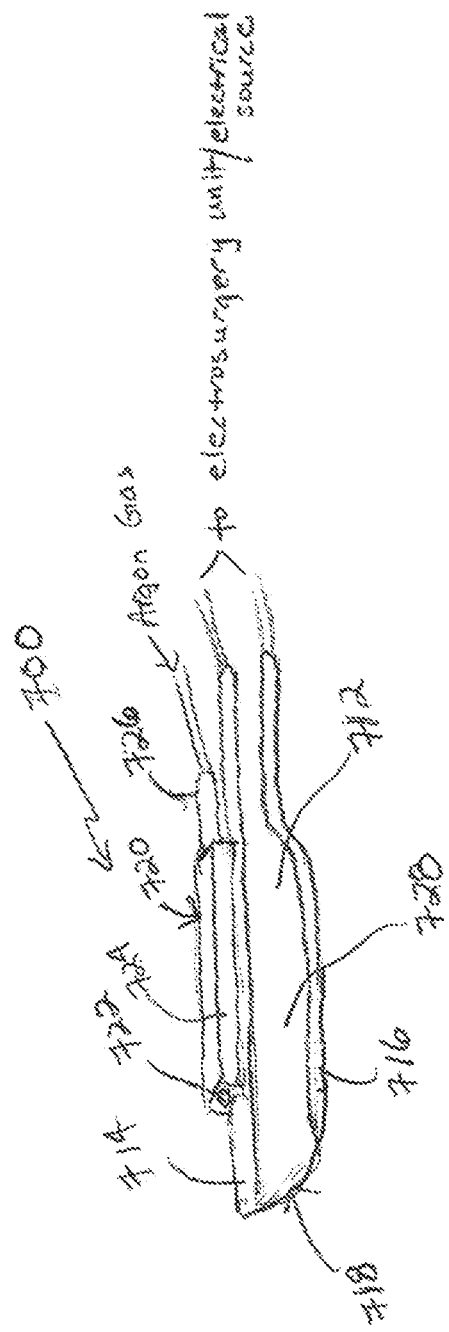

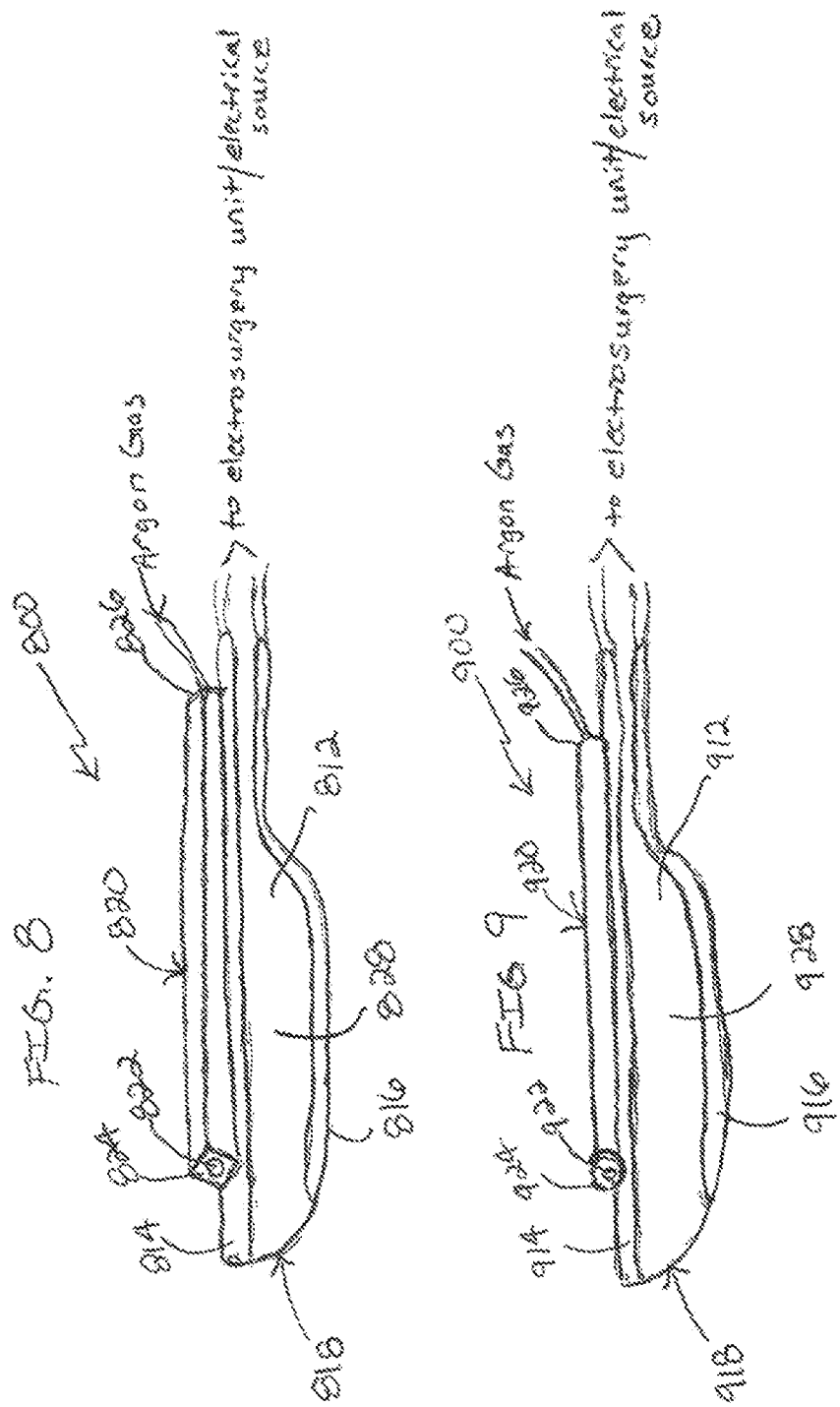

ELECTROSURGERY BLADES WITH ARGON BEAM CAPABILITY

FIELD OF INVENTION

The present invention is generally directed to electrosurgery blades, especially to electrosurgery blades having argon beam capability. More particularly, the present invention relates to an electrode blade assembly which includes an electrode blade and a non-conductive housing having an opening therethrough for administering argon gas where the non-conductive housing is positioned on or near a top of the electrode blade. The electrode blade can comprise many different configurations and may be a monopolar blade, a bipolar blade, and/or a bipolar blade that functions as a monopolar blade.

BACKGROUND OF THE INVENTION

Typical electrosurgical pencils use an electrode blade which functions as an active electrode for use in performing cutting and coagulation during electrosurgery and a return electrode usually comprising an adhesive for attachment to a patient's skin. When the electrosurgery pencil is activated, the RF energy circulates from the active electrode to the return electrode through the patient's body with the distance between the active and return electrodes being fairly significant. Electrosurgery uses a power supply and handpiece with one or more electrodes to provide high frequency, alternating current input at various voltages (200-10,000V) depending on the function, namely coagulation vs. cutting. For cutting, heat generated from continuous low voltage conduction can create a vapor pocket which vaporizes and explodes a small section of tissue which results in an incision. For coagulation, voltage is usually lower than in cut mode and the slower heating process results in less heat. As a result, no vapor pocket is formed so the tissue for the most part remains intact but with cells and vessels destroyed and sealed at the point of contact.

It is also common to use argon beam coagulators during electrosurgery. In argon beam coagulation (ABC), current is applied to tissue by a directed beam of ionized argon gas which causes a uniform and shallow coagulation surface thereby stopping blood loss. However, argon beam enhanced cutting may also be performed using application of an ionized argon gas.

At present, electrosurgery is often the best method for cutting and argon beam coagulation is often the best method for cessation of bleeding during surgery. Surgeons typically need to switch between argon beam coagulation and electrosurgery modes depending on what is happening during the surgery and what they need to achieve at a particular point in the surgery such as cutting, or making incisions in tissue, or stopping the bleeding at the surgical site.

However, since surgical tools and devices currently available to surgeons require switching between these two methods during the surgical procedure, there is a need for a surgical device or tool that enables a surgeon or user to utilize the best methods used for cutting and cessation of bleeding at the surgical site at the same time, or simultaneously, in addition to being able to use them separately. An electrosurgery blade having argon beam capability would meet this need. The electrosurgery blades with argon beam capability described with reference to the present invention could be used with an electrosurgery handpiece/pencil that does not have smoke evacuation capability but are also intended to be used with an electrosurgery handpiece/pencil that is capable of smoke evacuation during the electrosurgery procedure.

Such a surgical device or tool would enable the surgeon or user to increase both the efficiency and accuracy of the surgery by enabling the surgeon or user to perform both tissue cutting and coagulation at the same time without switching between modes or methods thereby decreasing operating time. In addition, performing both tissue cutting and coagulation at the same time along with smoke evacuation would enable the surgeon or user to more clearly view the surgical site to ensure accuracy during the procedure without the need to stop and switch modes in order to stop bleeding at the surgery site before being able to clearly see the surgical site.

SUMMARY OF THE INVENTION

The present invention is directed to an electrode assembly for use with an electrosurgery handpiece/pencil with smoke evacuation, or an electrosurgery handpiece/pencil without smoke evacuation, that includes an electrode blade and a non-conductive housing having an opening therethrough tor argon gas where the non-conductive housing is positioned on or near a top of the electrode blade.

The electrode blade may comprise a monopolar blade having a top, a bottom, and a side cutting edge where the non-conductive housing is positioned on the top of the electrode blade. In one exemplary embodiment, the non-conductive housing may comprise an elongated rectangular box shape having a top surface and a bottom surface where the bottom surface of the non-conductive housing is positioned adjacent to, and on top, of the top of the electrode blade.

In another exemplary embodiment of the present invention, the non-conductive housing may further comprise a tubular shaped member having an opening therethrough which is coextensive with the opening in the elongated rectangular box shaped portion of the housing to enable the connection of a source of argon gas to the non-conductive housing. In still another exemplary embodiment of the present invention, the non-conductive housing may completely comprise a tubular shaped member that is positioned adjacent to, and on top of, the top of the electrode blade.

The electrode blade may comprise stainless steel and/or copper and the non-conductive housing may comprise an inorganic, non-metallic solid material, such as a ceramic, for example. The electrode blade in the electrode assembly of the present invention may also have different configurations. For example, the top, the bottom, and the side cutting edge of the electrode blade may comprise a conductive material that surrounds a non-conductive portion of the electrode blade. In another example, the electrode blade may comprise a non-conductive portion located between the top and the bottom of the electrode blade where the top and the bottom of the electrode blade comprise a conductive material and the side cutting edge of the electrode blade comprises a non-conductive portion of the electrode blade.

In yet another exemplary embodiment of the invention, the electrode blade may comprise a bipolar electrode having an active electrode and a return electrode separated by a non-conductive portion or an insulator. The non-conductive housing may comprise any of the configurations previously described, namely an elongated rectangular box having an opening therethrough, a tubular shaped member having an opening therethrough, or an elongated rectangular box shaped portion having an opening therethrough and a tubular shaped portion having an opening therethrough where the elongated rectangular box shaped portion and the tubular shaped portion are connected to one another such that their respective openings are coextensive with one another. The non-conductive housing is positioned near a top of the bipolar electrode and, in one exemplary embodiment, the active electrode comprises the top of the bipolar electrode, the return electrode comprises the bottom of the bipolar electrode, and the non-conductive portion of the bipolar electrode comprises a side cutting edge of the bipolar electrode where the non-conductive housing is positioned adjacent to, and on top of, the active electrode.

The active and return electrodes may comprise stainless steel and/or copper and the non-conductive portion of the bipolar electrode and the non-conductive housing may each comprise an inorganic, non-metallic solid material. One example of such an inorganic, non-metallic solid material is a ceramic.

BRIEF DESCRIPTION OF THE DRAWINGS

The subject invention will hereinafter be described in conjunction with the appended drawing figures, wherein like numerals denote like elements, and FIG. 1 is a side perspective view of a first exemplary embodiment of the electrode assembly of the present invention having a monopolar electrode with argon beam capability;

FIG. 2 is a side perspective view of a second exemplary embodiment of the electrode assembly of the present invention having a monopolar electrode with argon beam capability;

FIG. 3 is a side perspective view of a third exemplary embodiment of the electrode assembly of the present invention having a monopolar electrode with argon beam capability;

FIG. 4 is a side perspective view of a fourth exemplary embodiment of the electrode assembly of the present invention having a monopolar electrode with argon beam capability;

FIG. 5 is a side perspective view of a filth exemplary embodiment of the electrode assembly of the present invention having a monopolar electrode with argon beam capability;

FIG. 6 is a side perspective view of a sixth exemplary embodiment of the electrode assembly of the present invention having a monopolar electrode with argon beam capability;

FIG. 7 is a side perspective view of a seventh exemplary embodiment of the electrode assembly of the present invention having a bipolar electrode with argon beam capability;

FIG. 8 is a side perspective view of an eighth exemplary embodiment of the electrode assembly of the present invention having a bipolar electrode with argon beam capability; and FIG. 9 is a side perspective view of a ninth exemplary embodiment of the electrode assembly of the present invention having a bipolar electrode with argon beam capability.

DETAILED DESCRIPTION OF EXEMPLARY EMBODIMENTS

The electrosurgery blade with argon capability of the present invention enables a user or surgeon to separately use an electrode for cutting and/or coagulation, separately use an argon beam for cutting and/or coagulation, or simultaneously use an electrode and an argon beam for cutting and/or coagulation. FIG. 1 shows a side perspective view of a first exemplary embodiment of an electrode assembly 10 with argon beam capability having a monopolar electrode in accordance with the present invention. Electrode assembly 10 includes an electrode blade 12 having a top 14, a bottom 16, and a side cutting edge 18, and a non-conductive housing 20 having an opening 22 therethrough for providing an ionized beam of argon gas. Non-conductive housing 20 includes a generally rectangular shaped box portion 24 that is connected to a generally tubular shaped portion 26, also having an opening therethrough, such that their respective openings are coextensive with one another for providing the ionized beam of argon gas. The generally tubular shaped portion 26 facilitates connection of the blade assembly 10 to a source of argon gas.

As shown in FIG. 1, a bottom surface of the non-conductive housing 20 is placed adjacent to, and on top of, the top 14 of electrode blade 12. Electrode blade 12 comprises a conductive material and may comprise, for example, stainless steel and/or copper. Non-conductive housing 20 may comprise an inorganic, non-metallic solid material such as a ceramic, for example.

FIG. 2 is a side perspective view of a second exemplary embodiment of the electrode assembly 200 of the present invention having a monopolar electrode with argon beam capability. Like the embodiment shown in FIG. 1, electrode assembly 200 includes an electrode blade 212 having a top 214, a bottom 216, and a side cutting edge 218, and a non-conductive housing 220 having an opening 222 therethrough for providing an ionized beam of argon gas. Non-conductive housing 220 includes a generally rectangular shaped box portion 224 that is connected to a generally tubular shaped portion 226, also having an opening therethrough, such that their respective openings are coextensive with one another for providing the ionized beam of argon gas. The generally tubular shaped portion 226 facilitates connection of the blade assembly 200 to a source of argon gas. In this embodiment, the top 214, the bottom 216, and the side cutting edge 218 of electrode blade 212 all comprise a conductive material that surrounds a non-conductive portion 228 of electrode blade 212. The conductive material that comprises the top 214, the bottom 216, and the side cutting edge 218 of the electrode blade may comprise stainless steel and/or copper. The non-conductive housing 220 and the non-conductive portion 228 of electrode blade 212 may each comprise an inorganic, non-metallic solid material such as a ceramic, for example.

A side perspective view of a third exemplary embodiment of an electrode assembly 300 with argon beam capability having a monopolar electrode in accordance with the present invention is shown in FIG. 3. Like the previously described embodiments, electrode assembly 300 includes an electrode blade 312 having a top 314, a bottom 316, and a side cutting edge 318, and a non-conductive housing 320 having an opening 322 therethrough for providing an ionized beam of argon gas. Non-conductive housing 320 includes a generally rectangular shaped box portion 324 that is connected to a generally tubular shaped portion 326, also having an opening therethrough, such that their respective openings are coextensive with one another for providing the ionized beam of argon gas. The generally tubular shaped portion 326 facilitates connection of the blade assembly 300 to a source of argon gas. In this third embodiment, the top 314 and the bottom 316 of electrode blade 312 comprise a conductive material and are separated by a non-conductive portion 328 of electrode blade 312 which also comprises the side cutting edge 318 of electrode blade 312. The conductive material that comprises the top 314 and the bottom 316 of the electrode blade 312 may comprise stainless steel and/or copper. The non-conductive housing 320 and the non-conductive portion 328 of electrode blade 312, including the side cutting edge 318 of electrode blade 312, may each comprise an inorganic, non-metallic solid material such as a ceramic, for example.

FIG. 4 is a side perspective view of a fourth exemplary embodiment of the electrode assembly 400 of the present invention having a monopolar electrode with argon beam capability. Like the embodiments described above with reference to FIGS. 1-3, electrode assembly 400 includes an electrode blade 412 having a top 414, a bottom 416, and a side cutting edge 418, and a non-conductive housing 420 having an opening 422 therethrough for providing an ionized beam of argon gas. Non-conductive housing 420 includes a generally rectangular shaped box portion 424 that is connected to a generally tubular shaped portion 426, also having an opening therethrough, such that their respective openings are coextensive with one another for providing the ionized beam of argon gas. The generally tubular shaped portion 426 facilitates connection of the blade assembly 400 to a source of argon gas, in this fourth embodiment, the top portion 414 of electrode blade 412 comprises a conductive material and the bottom portion 416 of electrode blade 412 comprises a non-conductive material. The side cutting edge 418 of electrode blade 412 comprises both a conductive material and a non-conductive material since the electrode blade comprises a top portion 414, which is conductive, that meets a bottom portion 416, that is non-conductive. The conductive material that comprises the top portion 414 of the electrode blade 412 may comprise stainless steel and/or copper. The non-conductive housing 420 and the non-conductive bottom portion 416 of electrode blade 412 may each comprise an inorganic, non-metallic solid material such as a ceramic, for example.

A side perspective view of a fifth exemplary embodiment of the electrode assembly 500 of the present invention that is similar to the first embodiment shown in FIG. 1 having a monopolar electrode with argon beam capability is shown in FIG. 5. Electrode assembly 500 includes an electrode blade 512 having atop 514, a bottom 516, and a side cutting edge 518, and a non-conductive housing 520 having an opening 522 therethrough for providing an ionized beam of argon gas. Non-conductive housing 520 comprises a generally rectangular shaped box having a first end 524 and a second end 526 that is connected to a source of argon gas. A bottom outer surface of the non-conductive housing 520 is placed adjacent to, and on top of, the ton 514 of electrode blade 512. Electrode blade 512 comprises a conductive material and may comprise, for example, stainless steel and/or copper. Non-conductive housing 520 may comprise an inorganic, non-metallic solid material such as a ceramic, for example. It will be understood by those skilled in the art that the configuration of the non-conductive housing 520 shown in FIG. 5 may be used with any of the configurations and embodiments of the electrode blades described and shown above with reference to FIGS. 2-4.

FIG. 6 is a side perspective view of a sixth exemplary embodiment of the electrode assembly 600 of the present invention having a monopolar electrode with argon beam capability that is similar to the first embodiment shown in FIG. 1. Electrode assembly 600 includes an electrode blade 612 having a top 614, a bottom 616, and a side cutting edge 618, and a non-conductive housing 620 having an opening 622 therethrough for providing an ionized beam of argon gas. Non-conductive housing 620 comprises a generally tubular shape having a first end 624 and a second end 626 that is connected to a source of argon gas. A bottom outer surface of the non-conductive housing 620 is placed adjacent to, and on top of, the top 614 of electrode blade 612. Electrode blade 612 comprises a conductive material and may comprise, for example, stainless steel and/or copper. Non-conductive housing 620 may comprise an inorganic, non-metallic solid material such as a ceramic, for example. It will be understood by those skilled in the art that the configuration of the non-conductive housing 620 shown In FIG. 6 may be used with any of the configurations and embodiments of the electrode blades described and shown above with reference to FIGS. 2-4.

FIG. 7 is a side perspective view of a seventh exemplary embodiment of the electrode assembly 700 of the present invention having a bipolar electrode with argon beam capability. Electrode assembly 700 includes an bipolar electrode blade 712 having an active electrode 714 and a return electrode 716 separated by a non-conductive portion 728, which includes a side cutting edge 718, and a non-conductive housing 720 having an opening 722 therethrough for providing an ionized beam of argon gas. Non-conductive housing 720 includes a generally rectangular shaped box portion 724 that is connected to a generally tubular shaped portion 726, also having an opening therethrough, such that their respective openings are coextensive with one another for providing the ionized beam of argon gas. The generally tubular shaped portion 726 facilitate connection of the blade assembly 700 to a source of argon gas. In this seventh embodiment, the active electrode 714 and the return electrode 716 comprise a conductive material such as stainless steel and/or copper. The non-conductive portion 728 of bipolar electrode blade 712, which also comprises the side cutting edge 718 of bipolar electrode blade 712, and the non-conductive housing 720 may each comprise an inorganic, non-metallic solid material such as a ceramic, for example.

A side perspective view of au eighth exemplary embodiment of the electrode assembly 800 of the present invention that is similar to the sixth embodiment shown in FIG. 6 having a bipolar electrode blade with argon beam capability is shown in FIG. 8. Electrode assembly 800 includes an bipolar electrode blade 812 having an active electrode 814 and a return electrode 816 separated by a non-conductive portion 828, which includes a side cutting edge 818, and a non-conductive housing 820 having an opening 822 therethrough for providing an ionized beam of argon gas. Non-conductive housing 820 comprises a generally rectangular shaped box having a first end 824 and a second end 826 that is connected to a source of argon gas. A bottom outer surface of the non-conductive housing 820 is placed adjacent to, and on top of, the active electrode 814 of bipolar electrode blade 812. In this eighth embodiment, the active electrode 814 and the return electrode 816 comprise a conductive material such as stainless steel and/or copper. The non-conductive portion 828 of bipolar electrode blade 812, which also comprises the side cutting edge 818 of bipolar electrode blade 812, and the non-conductive housing 820 may each comprise an inorganic, non-metallic solid material such as a ceramic, for example.

FIG. 9 is a side perspective view of a ninth exemplary embodiment of the electrode assembly 900 of the present invention having a bipolar electrode with argon beam capability. Electrode assembly 900 includes an bipolar electrode blade 912 having an active electrode 914 and a return electrode 916 separated by a non-conductive portion 928, which includes a side cutting edge 918, and a non-conductive housing 920 having an opening 922 therethrough for providing an ionized beam of argon gas. Non-conductive housing 920 comprises a generally tubular shape having a first end 924 and a second end 926 that is connected to a source of argon gas. A bottom outer surface of the non-conductive housing 920 is placed adjacent to, and on top of, the active electrode 914 of bipolar electrode blade 912. In this ninth embodiment, the active electrode 914 and the return electrode 916 comprise a conductive material such as stainless steel and/or copper. The non-conductive portion 928 of bipolar electrode blade 912, which also comprises the side cutting edge 918 of bipolar electrode blade 912, and the non-conductive housing 920 may each comprise an inorganic, non-metallic solid material such as a ceramic, for example.

Although the embodiments of the present invention show an electrode blade having a generally scalpel shape with an approximate 45 degree angle, it will be understood by those skilled in the art that the electrode blade in the electrode assembly of the present invention may take other shapes and forms without detracting from the purpose of the invention. For example, other shapes for the electrode blade may include, but are not limited to, an angled blade having one or more angles other than a generally 45 degree angle, a hook-shaped blade, and/or a paddle shaped blade.

With respect to the electrode assembly embodiments that include a bipolar electrode as shown in FIGS. 7-9, those skilled in the art will understand that both the active and return electrodes are connected to an electrosurgery unit to perform a completed circuit. When the electrosurgery unit is activated and the bipolar electrode touches the tissue of a patient, the circuit is closed through a very small portion of the patient's tissue between the active electrode and the return electrode. This shortened distance between the active electrode and the return electrode results in a decrease of the power requirement for cutting and coagulation from that needed with a monopolar electrode. The decreased distance between the active and return electrodes also results in decreasing the dangers associated with passing high voltages at high frequencies throughout a substantial portion of the patient's body, one of those risks being an increased possibility of burns to the patient.

Further, with respect to the embodiments shown in FIGS. 7-9 which include a bipolar electrode, it will be understood by those skilled in the art that the active electrode and return electrode described in those embodiments may be reversed such that the active and return electrodes are on opposite sides of the non-conductive portion of the blade than those on which they are depicted in the Figures. It will also be understood by those skilled in the art that the bipolar electrodes shown in FIGS. 7-9 are capable of exhibiting both bipolar and monopolar functioning in conjunction with an electrosurgery unit.

Finally, as previously mentioned, it will be understood by those skilled in the art that the electrode assembly of the present invention which includes an electrode with argon beam capabilities can be used to perform cutting and/or coagulation separately or simultaneously with either or both the electrode or argon beam. Further, the electrode assembly of the present invention which includes an electrode with argon beam capabilities may be used in in both an electrosurgery handpiece that does have a means for smoke evacuation and an electrosurgery handpiece that does not have means for smoke evacuation.

The detailed description of exemplary embodiments of the invention herein shows various exemplary embodiments of the invention. These exemplary embodiments and modes are described in sufficient detail to enable those skilled in the art to practice the invention and are not intended to limit the scope, applicability, or configuration of the invention in any way. Rather, the following disclosure is intended to teach both the implementation of the exemplary embodiments and modes and any equivalent modes or embodiments that are known or obvious to those reasonably skilled in the art. Additionally, all included examples are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

Unless specifically noted, it is the Applicant's intent that the words and phrases in the specification and the claims be given the commonly accepted generic meaning or an ordinary and accustomed meaning used by those of ordinary skill in the applicable arts. In the instance where these meanings differ, the words and phrases in the specification and the claims should be given the broadest possible, generic meaning. If any other special meaning is intended for any word or phrase, the specification will clearly state and define the special meaning.

The invention claimed is:

1. An electrode assembly for use in an electrosurgery pencil comprising;
   an electrode blade having a generally scalpel shape with a planar top and an opposite sharp bottom that includes a side cutting edge located opposite an end of the electrode blade that is connectable to an energy source; and
   a non-conductive housing having an opening therethrough positioned near the planar top of said electrode blade wherein a total length of the non-conductive housing is positioned adjacent to and on the planar top of the electrode blade such that the total length of the non-conductive housing is touching the electrode blade and at least a portion of the planar top of the electrode blade extends beyond the non-conductive housing near the side cutting edge of the electrode blade.

2. The electrode assembly of claim 1 wherein the non-conductive housing comprises an elongated rectangular box shape having a top surface and a bottom surface.

3. The electrode assembly of claim 2 wherein the bottom surface of the non-conductive housing is positioned adjacent to and on top of the top of the electrode blade.

4. The electrode assembly of claim 2 wherein the non-conductive housing further comprises a tubular member.

5. The electrode assembly of claim 1 wherein the non-conductive housing comprises a tubular shaped member.

6. The electrode assembly of claim 1 wherein the electrode blade comprises at least one of a stainless steel and a copper.

7. The electrode assembly of claim 1 wherein the top, the bottom, and the side cutting edge of the electrode blade comprise a conductive material that surrounds a non-conductive portion of the electrode blade.

8. The electrode assembly of claim 7 wherein the conductive material comprises at least one of a stainless steel and a copper and the non-conductive portion of the electrode blade comprises an inorganic, non-metallic solid material.

9. The electrode assembly of claim 8 wherein the non-conductive housing comprises a ceramic material.

10. The electrode assembly of claim 1 wherein the electrode blade comprises a non-conductive portion located between the planar top and the sharp bottom of the electrode blade wherein the planar top and the sharp bottom of the electrode blade comprise a conductive material and the side cutting edge comprises a part of the non-conductive portion of the electrode blade.

11. The electrode assembly of claim 10 wherein the conductive material comprise at least one of a stainless steel and a copper and the non-conductive portion of the electrode blade comprises an inorganic, non-metallic solid material.

12. The electrode assembly of claim 11 wherein the inorganic, non-metallic solid material comprises a ceramic material.

13. The electrode assembly of claim 1 wherein the non-conductive housing comprises an inorganic, non-metallic solid material.

14. The electrode assembly of claim 13 wherein the non-conductive housing comprises a ceramic material.

15. An electrode assembly for use in an electrosurgery pencil comprising:
   a bipolar electrode blade having a generally scalpel shape with a top planar active electrode and a sharp bottom return electrode separated by a non-conductive portion which includes a side cutting edge; and
   a non-conductive housing having an opening therethrough positioned adjacent to and on top of the top planar active electrode of the bipolar electrode blade such that the a total length of the non-conductive housing is touching the top planar active electrode of the bipolar electrode blade and at least a portion of the top planar active electrode of the electrode blade extends beyond the non-conductive housing.

16. The electrode assembly of claim 15 wherein the non-conductive portion of the bipolar electrode that includes the side cutting edge is located on an end of the bipolar electrode blade that is opposite an end of the bipolar electrode blade that is connectable to an energy source.

17. The electrode assembly of claim 15 wherein the top planar active electrode and the sharp bottom return electrode comprise at least one of a stainless steel and a copper and the non-conductive portion of the bipolar electrode blade and the non-conductive housing each comprise an inorganic, non-metallic solid material.

18. The electrode assembly of claim 17 wherein the inorganic, non-metallic solid material comprises a ceramic.

19. The electrode assembly of claim 15 wherein the non-conductive housing comprises an elongated rectangular box shape having a top surface and a bottom surface.

20. The electrode assembly of claim 19 wherein the non-conductive housing further comprises a tubular member.

21. The electrode assembly of claim 15 wherein the non-conductive housing comprises a tubular shaped member.

22. An electrode assembly for use in an electrosurgery pencil comprising:
   an electrode blade having a generally scalpel shape with a planar top and a sharp bottom opposite the planar top that includes a non-conductive side cutting edge located between the planar top and the sharp bottom of the electrode blade; and
   a non-conductive housing having an opening therethrough positioned adjacent to and touching the planar top of the electrode blade wherein a total height of the non-conductive housing is less than a height of the electrode blade and at least a portion of the planar top of the electrode blade extends beyond the non-conductive housing.

23. The electrode assembly of claim 22 wherein the non-conductive housing comprises a tubular shaped member.

* * * * *